United States Patent
Mazor et al.

(10) Patent No.: US 9,632,043 B2
(45) Date of Patent: Apr. 25, 2017

(54) METHOD FOR ACCURATELY DETERMINING THE THICKNESS AND/OR ELEMENTAL COMPOSITION OF SMALL FEATURES ON THIN-SUBSTRATES USING MICRO-XRF

(71) Applicant: JORDAN VALLEY SEMICONDUCTORS LTD., Migdal HaEmek (IL)

(72) Inventors: Isaac Mazor, Haifa (IL); Fouad Atrash, Akko (IL); Alex Tokar, Haifa (IL); Olga Ostrovsky, Haifa (IL)

(73) Assignee: BRUKER JV ISRAEL LTD., Migdal Haemek (IL)

( * ) Notice: Subject to any disclaimer, the term of this patent is extended or adjusted under 35 U.S.C. 154(b) by 36 days.

(21) Appl. No.: 14/708,323

(22) Filed: May 11, 2015

(65) Prior Publication Data
US 2015/0330921 A1   Nov. 19, 2015

Related U.S. Application Data

(60) Provisional application No. 61/992,234, filed on May 13, 2014.

(51) Int. Cl.
*G01N 23/00* (2006.01)
*G01N 23/207* (2006.01)
(Continued)

(52) U.S. Cl.
CPC ....... *G01N 23/2076* (2013.01); *G01N 23/223* (2013.01); *G01N 2223/6116* (2013.01); *H01L 22/12* (2013.01)

(58) Field of Classification Search
CPC ............. G01N 23/2076; G01N 23/223; G01N 2223/6116; H01L 22/12
(Continued)

(56) References Cited

U.S. PATENT DOCUMENTS 2,711,480 A * 6/1955 Friedman ............. G01N 23/203
378/50
3,256,431 A   6/1966 Frazer
(Continued)

FOREIGN PATENT DOCUMENTS

JP    6186344 A    7/1994
JP    06273146 A    9/1994
(Continued)

OTHER PUBLICATIONS

Singer, "Copper CMP: Taking aim at Dishing", Semiconductor International (www.reed-electronics.com/semiconductor/), 4 pages, Oct. 1, 2004.
(Continued)

*Primary Examiner* — Michael Maskell
(74) *Attorney, Agent, or Firm* — D. Kligler Services Ltd.

(57) ABSTRACT

A method for X-ray Fluorescence (XRF) analysis includes directing an X-ray beam onto a sample and measuring an XRF signal excited from the sample, in a reference measurement in which the sample includes one or more first layers formed on a substrate, and in a target measurement after one or more second layers are formed on the substrate in addition to the first layers, so as to produce a reference XRF spectrum and a target XRF spectrum, respectively. A contribution of the first layers to the target XRF spectrum is reduced using the reference XRF spectrum. A parameter of at least one of the second layers is estimated using the target XRF spectrum in which the contribution of the first layers has been reduced.

20 Claims, 3 Drawing Sheets

(51) Int. Cl.
*G01N 23/223* (2006.01)
*H01L 21/66* (2006.01)

(58) Field of Classification Search
USPC .................................. 250/306, 307, 310, 311
See application file for complete search history.

(56) References Cited

U.S. PATENT DOCUMENTS

| | | |
|---|---|---|
| 3,581,087 A | 5/1971 | Brinkerhoff |
| 3,754,138 A * | 8/1973 | Kurstedt, Jr. .......... B29D 30/38 250/302 |
| 3,919,548 A | 11/1975 | Porter |
| 3,980,568 A | 9/1976 | Pitchford et al. |
| 3,984,680 A | 10/1976 | Smith |
| 4,048,496 A | 9/1977 | Albert |
| 4,085,329 A | 4/1978 | McCoy et al. |
| 4,169,228 A | 9/1979 | Briska et al. |
| 4,377,869 A * | 3/1983 | Venalainen .......... G01N 23/223 378/210 |
| 4,446,568 A | 5/1984 | Williams et al. |
| 4,551,905 A | 11/1985 | Chao et al. |
| 4,590,603 A | 5/1986 | Relihan et al. |
| 4,710,259 A | 12/1987 | Howe et al. |
| 4,718,075 A | 1/1988 | Horn |
| 4,725,963 A | 2/1988 | Taylor et al. |
| 4,847,882 A | 7/1989 | Knoth et al. |
| 4,852,135 A | 7/1989 | Anisovich et al. |
| 4,916,720 A | 4/1990 | Yamamoto et al. |
| 4,989,226 A | 1/1991 | Woodbury et al. |
| 5,151,588 A | 9/1992 | Kiri et al. |
| 5,365,563 A | 11/1994 | Kira et al. |
| 5,385,867 A | 1/1995 | Kumakhov |
| 5,425,066 A | 6/1995 | Takahashi et al. |
| 5,481,109 A | 1/1996 | Ninomiya et al. |
| 5,497,008 A | 3/1996 | Kumakhov |
| 5,574,284 A | 11/1996 | Farr |
| 5,619,548 A | 4/1997 | Koppel |
| 5,740,226 A | 4/1998 | Komiya et al. |
| 5,742,658 A | 4/1998 | Tiffin et al. |
| 5,778,039 A | 7/1998 | Hossain et al. |
| 5,877,498 A | 3/1999 | Sugimoto et al. |
| 5,893,758 A | 4/1999 | Sandhu et al. |
| 5,900,645 A | 5/1999 | Yamada |
| 5,909,276 A | 6/1999 | Kinney et al. |
| 5,923,720 A | 7/1999 | Barton et al. |
| 5,937,026 A | 8/1999 | Satoh |
| 5,949,847 A | 9/1999 | Terada et al. |
| 5,963,329 A | 10/1999 | Conrad et al. |
| 6,001,736 A | 12/1999 | Kondo et al. |
| 6,040,095 A | 3/2000 | Enichen et al. |
| 6,041,095 A | 3/2000 | Yokhin |
| 6,041,098 A | 3/2000 | Touryanski et al. |
| 6,108,398 A | 8/2000 | Mazor et al. |
| 6,173,036 B1 | 1/2001 | Hossain et al. |
| 6,192,103 B1 | 2/2001 | Wormington et al. |
| 6,226,347 B1 | 5/2001 | Golenhofen |
| 6,226,349 B1 | 5/2001 | Schuster et al. |
| 6,266,389 B1 | 7/2001 | Murayama et al. |
| 6,345,086 B1 | 2/2002 | Ferrandino et al. |
| 6,351,516 B1 | 2/2002 | Mazor et al. |
| 6,381,303 B1 | 4/2002 | Vu et al. |
| 6,389,102 B2 | 5/2002 | Mazor et al. |
| 6,453,002 B1 | 9/2002 | Mazor et al. |
| 6,453,006 B1 | 9/2002 | Koppel et al. |
| 6,507,634 B1 | 1/2003 | Koppel et al. |
| 6,512,814 B2 | 1/2003 | Yokhin et al. |
| 6,556,652 B1 | 4/2003 | Mazor et al. |
| 6,639,968 B2 | 10/2003 | Yokhin et al. |
| 6,643,354 B2 | 11/2003 | Koppel et al. |
| 6,680,996 B2 | 1/2004 | Yokhin et al. |
| 6,704,661 B1 | 3/2004 | Opsal et al. |
| 6,711,232 B1 | 3/2004 | Janik |
| 6,744,850 B2 | 6/2004 | Fanton et al. |
| 6,744,950 B2 | 6/2004 | Aleksoff |
| 6,750,952 B2 | 6/2004 | Grodnensky et al. |
| 6,754,304 B1 | 6/2004 | Kumakhov |
| 6,754,305 B1 | 6/2004 | Rosencwaig et al. |
| 6,771,735 B2 | 8/2004 | Janik et al. |
| 6,810,105 B2 | 10/2004 | Nasser-Ghodsi et al. |
| 6,823,043 B2 | 11/2004 | Fewster et al. |
| 6,879,051 B1 | 4/2005 | Singh et al. |
| 6,890,575 B2 | 5/2005 | Beauregard et al. |
| 6,891,627 B1 | 5/2005 | Levy et al. |
| 6,895,075 B2 | 5/2005 | Yokhin et al. |
| 6,947,520 B2 | 9/2005 | Yokhin et al. |
| 6,977,986 B1 | 12/2005 | Beanland et al. |
| 7,023,954 B2 | 4/2006 | Rafaeli et al. |
| 7,062,013 B2 | 6/2006 | Berman et al. |
| 7,068,753 B2 | 6/2006 | Berman et al. |
| 7,071,007 B2 | 7/2006 | Tseng et al. |
| 7,103,142 B1 | 9/2006 | Agnihotry et al. |
| 7,110,491 B2 | 9/2006 | Mazor et al. |
| 7,120,228 B2 | 10/2006 | Yokhin et al. |
| 7,130,376 B2 | 10/2006 | Berman et al. |
| 7,183,547 B2 | 2/2007 | Yun et al. |
| 7,245,695 B2 | 7/2007 | Mazor et al. |
| 7,551,719 B2 | 6/2009 | Yokhin et al. |
| 7,600,916 B2 | 10/2009 | Yokhin et al. |
| 7,649,978 B2 | 1/2010 | Mazor et al. |
| 7,653,174 B2 | 1/2010 | Mazor et al. |
| 7,804,934 B2 | 9/2010 | Agnihotri et al. |
| 7,968,444 B2 | 6/2011 | Luo et al. |
| 2001/0028699 A1 | 10/2001 | Iwasaki |
| 2001/0043668 A1 | 11/2001 | Hayashi et al. |
| 2002/0097837 A1 | 7/2002 | Fanton et al. |
| 2002/0110218 A1 | 8/2002 | Koppel et al. |
| 2003/0012337 A1 | 1/2003 | Fewster et al. |
| 2003/0128809 A1 | 7/2003 | Umezawa et al. |
| 2003/0157559 A1 | 8/2003 | Omote et al. |
| 2004/0052330 A1 | 3/2004 | Koppel et al. |
| 2004/0109531 A1 | 6/2004 | Yokhin et al. |
| 2004/0131151 A1 | 7/2004 | Berman et al. |
| 2004/0156474 A1 | 8/2004 | Yokhin et al. |
| 2004/0218717 A1 | 11/2004 | Koppel et al. |
| 2004/0267490 A1 | 12/2004 | Opsal et al. |
| 2005/0282300 A1 | 12/2005 | Yun et al. |
| 2006/0062350 A1 | 3/2006 | Yokhin et al. |
| 2006/0227931 A1 | 10/2006 | Mazor et al. |
| 2006/0274886 A1 | 12/2006 | Mazor et al. |
| 2008/0021665 A1 | 1/2008 | Vaughnn |
| 2008/0049895 A1 | 2/2008 | Agnihotri et al. |
| 2008/0095309 A1 * | 4/2008 | Puusaari .............. G01N 23/223 378/44 |
| 2008/0159475 A1 | 7/2008 | Mazor et al. |
| 2013/0089178 A1 | 4/2013 | Mazor et al. |
| 2014/0286473 A1 * | 9/2014 | Tokar ................... G01N 23/223 378/43 |

FOREIGN PATENT DOCUMENTS

| | | |
|---|---|---|
| JP | 2006283585 A | 10/1994 |
| JP | 07019844 A | 1/1995 |
| JP | 7128259 A | 5/1995 |
| JP | 09308339 A | 12/1997 |
| JP | 10048398 A | 2/1998 |
| JP | 10318949 A | 12/1998 |
| JP | 2004003959 A | 1/2004 |
| JP | 2004151004 A | 5/2004 |
| WO | 92/08235 A1 | 5/1992 |

OTHER PUBLICATIONS

Reed Electronics Group, Semiconductor International, "Webcast Equipment Auction" (www.reed-electronics.com/semiconductor/), 2 pages, Dec. 15, 2005.

Dane et al., "Application of Genetic Algorithms for Characterization of Thin Layered Materials by Glancing Incidence X-Ray Reflectometry", Physica B 253, pp. 254-268, Feb. 26, 1998.

Kozaczek et al., "X-Ray Diffraction Metrology for 200 mm Process Qualification and Stability Assessment", Advanced Metallization Conference, Montreal, Canada, 6 pages, Oct. 8-11, 2001.

(56) References Cited

OTHER PUBLICATIONS

Powell et al., "X-Ray Diffraction and Reflectivity Characterization of SiGe Superlattice Structures", Semiconductor Science and Technology Journal, vol. 7, No. 5, pp. 627-631, United Kingdom, 1992.
Neissendorfer et al., "The Energy—Dispersive Reflectorneter / Diffractometer at BESSY-I", Measurement Science and Technology Journal, vol. 10, No. 5, pp. 354-361, year 1999.
Ulyanenkov, "Introduction to High Resolution X-Ray Diffraction", Workshop on X-Ray Characterization to Thin Layers, 50 pages, Uckley, May 21-23, 2003.
Huang et al., "Characterization of Single and Multiple-Layer Films by X-Ray Reflectometry", Advances in X-Ray Analysis, vol. 35, pp. 137-142, New York, USA, 1992.
EX-6500 Advanced EDXRF Spectrometer Manufactures by Jordan Valley Semiconductors, 2 pages, year 2000.
Lengeler, "X-Ray Reflection, a New Tool for Investigating Layered Structures and Interfaces", Advances in X-Ray Analysis, Plenum Press, vol. 35, pp. 127-135, New York, USA, 1992.
Lankosz et al., "Research in Quantitative X-Ray Fluorescence Microanalysis of Patterned This Films", Advances in X-Ray Analysis, vol. 43, pp. 497-503, year 1999.
Parrill et al., "GISAXS—Glancing Incidence Small Angle X-Ray Scattering", Journal de Physique IV, supplement to Journal de Physique I, vol. 3, pp. 411-417, Dec. 1993.
Bowen et al., "X-Ray Metrology by Diffraction and Reflectivity", 2000 International Conference on Characterization and Metrology for ULSI Technology, NIST, Gaithersburg, Maryland, USA, pp. 570-579, Jun. 26-29, 2000.
Naudon et al., "New Apparatus for Grazing X-Ray Reflectometry in the Angle-Resolved Dispersive Mode", Journal of Applied Crystallography, vol. 22, pp. 460-464, year 1989.
X-Ray Optical Systems, Inc., "Monolithic Polycapillary Lens Information", Albany, USA, 1 page, Dec. 29, 1998.
Markowicz et al., "Quantification in XRF Analysis of Intermediate-Thickness Samples", Handbook of X-Ray Spectrometry, 2nd edition, chapter 6, pp. 408-431, Antwerp, Belgium, CRC Press 2001.
U.S. Appl. No. 11/018,352, Office Action dated Feb. 8, 2006.
U.S. Appl. No. 11/889,337, Office Action dated Jul. 24, 2008.
U.S. Appl. No. 11/018,352, Office Action dated Oct. 24, 2005.
U.S. Appl. No. 11/487,433, Office Action dated May 29, 2008.
U.S. Appl. No. 12/003,215, Office Action dated Apr. 1,2009.
U.S. Appl. No. 11/103,071, Office Action dated Oct. 5, 2006.
U.S. Appl. No. 09/028,588, Office Action dated Jun. 4, 1999.
Jones et al., "Small Angle X-Ray Scattering for sub-100 nm Pattern Characterization", Journal of Applied Physics, vol. 83, No. 19, pp. 4059-4061, Nov. 10, 2003.
Hu et al., "Small Angle X-Ray Scattering Metrology for Sidewall Angle and Cross Section of Nanometer Scale Line Gratings", Journal of Applied Physics, vol. 96, No. 4, pp. 1983-1987, Aug. 15, 2004.
Wu et al., "Small Angle Neutron Scattering Measurements of Nanoscale Lithographic Features", Polymer Preprints, vol. 42, No. 1, pp. 265-266, year 2001.
Kojima et al., "Structural Characterization of Thin Films by X-Ray Reflectivity", Rigaku Journal, vol. 16, No. 2, pp. 31-41, year 1999.
X-Ray Optical Systems, Inc., "Micro X-Ray Fluorescence with Focusing Polycapillary Optics", Application Note 102, 2 pages, USA, Jun. 12, 2002.
Guerault, "Specular Reflectivity and Off-Specular Scattering: Tools for Roughness Investigation", Institute Voor Kern-en Stralingsfysica, 15 pages, Dec. 15, 2000.
Wiener et al., "Characterization of Titanium Nitride Layers by Grazing—Emission X-Ray Fluorescence Spectrometry", Applied Surface Science, vol. 125, pp. 129-136, Elsevier Science B.V., year 1999.
Hayashi et al., "Refracted X-Rays Propagating Near the Surface Under Grazing Incidence Condition", Spectrochimica Acta, Part B 54, pp. 227-230, year 1999.
Di-Fonzo et al., "Non-Destructive Determination of Local Strain with 100-Nanometre Spatial Resolution", Letters to Nature, vol. 403, pp. 638-640, Feb. 10, 2000.
Agnihotri, U.S. Appl. No. 11/610,174, "Accurate Measurement of Layer Dimensions using XRF", filed Dec. 13, 2006 (abandoned).
Japan Patent Application 2007-340602, Office Action dated Apr. 24, 2012.
Leng et al., "Simultaneous Measurement of Six Layers in a Silicon on Insulator Film Stack using Spectrophotometry and Beam Profile Reflectometry", Journal of Applied Physics, vol. 81, No. 8, pp. 3570-3578, Apr. 15, 1997.
Boer, "Calculation of X-Ray Fluorescence Intensities from Bulk and Multilayer Samples", X-Ray Spectrometry, vol. 19, pp. 145-154, 1990.
Mantler, "X-ray fluorescence analysis of multiple-layer films", Analytica chimica acta, vol. 188, pp. 25-35, 1986.
Patterson, "Transforming mobile electronics with copper pillar interconnect", Advancing microelectronics, vol. 39, No. 3, pp. 18-24, May/Jun. 2012.
Beckhoff et al, "Handbook of Practical X-Ray Fluorescence Analysis", Springer-Verlag, Berlin, Heidelberg , pp. 1-30, 2006.
U.S. Appl. No. 13/647,408 Official Action dated Jul. 25, 2014.
Boer et al., "How Accurate is the Fundamental Parameter approach? XRF Analysis of Bulk and Multilayer Samples", X-Ray Spectrometry, vol. 22, pp. 33-38, 1993.
U.S. Appl. No. 13/647,408 Office Action dated Oct. 30, 2014.
U.S. Appl. No. 13/647,408 Office Action dated Jul. 8, 2015.
U.S. Appl. No. 14/222,635 Office Action dated Dec. 7, 2015.

* cited by examiner

METHOD FOR ACCURATELY DETERMINING THE THICKNESS AND/OR ELEMENTAL COMPOSITION OF SMALL FEATURES ON THIN-SUBSTRATES USING MICRO-XRF

CROSS-REFERENCE TO RELATED APPLICATIONS

This application claims the benefit of U.S. Provisional Patent Application 61/992,234, filed May 13, 2014, whose disclosure is incorporated herein by reference.

FIELD OF THE INVENTION

The present invention relates generally to X-ray analysis, and particularly to methods and systems for analysis of thin layers on substrates.

BACKGROUND OF THE INVENTION

X-ray fluorescence (XRF) measurement, and specifically X-ray microfluorescence (i.e., X-ray fluorescence using sub-millimeter, focused excitation beams), is gaining increasing attention as a method for testing semiconductor wafers. XRF itself is a well-known technique for determining dimensions, such as thickness, and elemental composition of a sample. XRF analyzers generally include an X-ray source, which irradiates the sample, and an X-ray detector, for detecting the X-ray fluorescence emitted by the sample in response to the irradiation. Each element in the sample emits X-ray fluorescence in energy bands that are characteristic of the element. The detected X-ray fluorescence is analyzed to find the energies or, equivalently, the wavelengths and respective intensities of the detected photons, and the qualitative and/or quantitative thickness and composition of the sample is determined based on this analysis.

The use of X-ray microfluorescence for testing semiconductor wafers is described in various publications. Examples of prior art techniques are provided below.

U.S. Pat. No. 6,108,398, whose disclosure is incorporated herein by reference, describes an XRF analyzer and a method for analyzing a sample. The analyzer includes an X-ray beam generator, which generates an X-ray beam incident at a spot on the sample and creates a plurality of fluorescent X-ray photons. An array of semiconductor detectors is arranged around the spot so as to capture the fluorescent X-ray photons. The analyzer produces electrical pulses suitable for analysis of the sample.

U.S. Pat. No. 6,351,516, whose disclosure is incorporated herein by reference, describes a non-destructive method for testing the deposition and/or the removal of a material within a recess on the surface of a sample. An excitation beam is directed onto a region of the sample in a vicinity of the recess, and an intensity of X-ray fluorescence emitted from the region is measured. A quantity of the material that is deposited within the recess is determined responsively to the measured intensity.

Another application of X-ray microfluorescence is described by Lankosz et al., in a paper entitled "Research in Quantitative X-ray Fluorescence Microanalysis of Patterned Thin Films," Advances in X-ray Analysis 43 (1999), pages 497-503, which is incorporated herein by reference. The authors describe a method for X-ray fluorescence microanalysis using a collimated micro-beam. The method is applied for testing the thickness and uniformity of thin films prepared by ion sputtering techniques.

SUMMARY OF THE INVENTION

An embodiment of the present invention that is described herein provides a method for X-ray Fluorescence (XRF) analysis including directing an X-ray beam onto a sample and measuring an XRF signal excited from the sample, in a reference measurement in which the sample includes one or more first layers formed on a substrate, and in a target measurement after one or more second layers are formed on the substrate in addition to the first layers, so as to produce a reference XRF spectrum and a target XRF spectrum, respectively. A contribution of the first layers to the target XRF spectrum is reduced using the reference XRF spectrum. A parameter of at least one of the second layers is estimated using the target XRF spectrum in which the contribution of the first layers has been reduced.

In some embodiments, the parameter includes a thickness of at least one of the second layers. In other embodiments, the parameter includes an elemental composition of at least one of the second layers. In yet other embodiments, the first and second layers are formed on respective first and second opposite surfaces of the substrate, such that the second surface faces the X-ray beam.

In an embodiment, the contribution of the first layers to the target XRF spectrum is caused by excitation in the first layers by the X-ray beam after penetrating the substrate. In another embodiment, the first or second layers include Under Bump Metallization (UBM) layers or bumps. In yet another embodiment, reducing the contribution of the first layers includes estimating a contribution of a first spectral line in the reference XRF spectrum to an intensity of a second spectral line in the target XRF spectrum that overlaps the first spectral line.

In some embodiments, estimating the contribution of the first spectral line includes estimating an attenuation of the first spectral line by the second layers. In other embodiments, estimating the attenuation includes iteratively evaluating the attenuation as a function of respective estimated parameters of the second layers. In yet other embodiments, iteratively evaluating the attenuation includes, in an initial iteration, evaluating the function using nominal parameters of the second layers.

There is additionally provided, in accordance with an embodiment of the present invention, an apparatus for X-ray Fluorescence (XRF) analysis including an X-ray source, a detector and a processor. The X-ray source is configured to direct an X-ray beam onto a sample. The detector is configured to measure an XRF signal excited from the sample. The processor is configured to produce a reference XRF spectrum and a target XRF spectrum, respectively, from a reference measurement of the detector in which the sample includes one or more first layers formed on a substrate, and from a target measurement of the detector after one or more second layers are formed on the substrate in addition to the first layers, to reduce a contribution of the first layers to the target XRF spectrum using the reference XRF spectrum, and to estimate a parameter of at least one of the second layers using the target XRF spectrum in which the contribution of the first layers has been reduced.

The present invention will be more fully understood from the following detailed description of the embodiments thereof, taken together with the drawings in which:

DETAILED DESCRIPTION OF EMBODIMENTS

Overview

X-ray fluorescence (XRF) techniques are used for thickness and elemental composition measurements during manufacturing processes of semiconductor devices. In some semiconductor devices, one or more metal layers having a thickness on the order of 10 μm or less are formed on both sides of a substrate that has a typical thickness of about 100 μm. The layers on both sides of the substrate may comprise similar materials, such as copper, nickel, gold, palladium, silver or tin.

Measuring the thicknesses and/or composition of the layers is based on analyzing spectral lines in the spectrum of the XRF signals excited from the layers. In some practical scenarios, the detection of the XRF spectrum excited by the layers on one surface of the substrate may also contain a contribution from the XRF spectrum excited by the layers on the opposite surface. This interference is particularly noticeable when the substrate is thin (sufficiently thin for the X-ray beam to penetrate it), and when layers on both sides have common elemental composition (causing XRF spectral lines to overlap).

Thus, when measuring the thicknesses of the layers formed on the upper surface, and/or the layer composition, the XRF signals excited from the layers formed on the lower surface may interfere with the XRF signals excited from the layers formed on the upper surface, thus limiting the estimation accuracy of measuring the thicknesses or composition of the layers formed on the upper surface. Similar interference may occur when measuring the thicknesses and composition of the layers on the lower surface.

Embodiments of the present invention that are described herein provide improved methods and systems for estimating parameters of thin films layered on one surface of a thin substrate by evaluating and reducing interfering contribution of XRF signals excited from the other surface of the same substrate. The embodiments described herein refer mainly to estimation of layer thickness, but the disclosed techniques can be used for estimation of other suitable parameters, such as layer elemental composition.

In some embodiments, measuring the thicknesses and/or compositions of the layers on one side is carried out in two measurement steps. In the first measurement step, the spectrum of the XRF signal excited from a substrate that comprises layers on the lower surface is measured before the formation of the layers on the upper surface, and is saved as an evaluated background spectrum. In a second measurement step, a second XRF spectrum is performed after the substrate already comprises one or more of the layers on the upper surface. The contribution of the layers on the lower surface to the XRF spectrum excited in the second measurement is reduced using XRF spectrum obtained in the first measurement, so as to improve the estimation accuracy of the thicknesses and/or composition of the layers on the upper surface.

The layers on the substrate may have different geometric configurations. In some cases, the geometric attributes (e.g., the thickness or width) of the layers on the upper surface may attenuate the intensity of the background component of the spectrum in the second measurement step relative to the evaluated background spectrum, and thus, may reduce the accuracy of the estimated thicknesses and compositions. In other embodiments nominal thicknesses and/or compositions of the layers on the upper surface may be used to evaluate the attenuation of the intensity of the background component in the excited spectrum due to the geometric configuration of the layers on the upper surface.

In yet other embodiments, an iterative process may be applied to improve the accuracy of the estimated thicknesses and/or compositions of the layers on the upper surface. The estimated thicknesses or compositions of the layers on the upper surface may be used to re-evaluate the background spectrum. The re-evaluated background spectrum may be used to re-estimate the thicknesses and/or compositions of the layers more accurately. This iterative process may repeat until reaching a desired accuracy. In an embodiment, a convergence threshold value ϵ may be used to control the iterations loop. The iteration loop is thus terminated when the absolute value of the difference between the estimated thicknesses and/or compositions obtained in the most recent two iterations is smaller than ϵ. Other suitable criteria for terminating the iteration loop can also be used.

The disclosed techniques are useful to provide accurate feedback for layer deposition systems during semiconductor (and other electronic components) manufacturing processes. Improved control of critical parameters, such as thickness and elemental composition, reduces process variations and thus, improves the electrical performance of the manufactured electronic devices.

For the sake of clarity and convenience of description, the embodiments that are described below refer to layers of Under Bump Metallization (UBM) formed on a wafer and the solder bumps formed on the UBM that are used to provide electrical contacts as part of a Wafer Level Packaging (WLP) technology. The disclosed techniques, however, may be similarly implemented using other types of manufacturing processes, electronic substrates and devices, materials, and geometric configurations.

System Description

Figure 1:
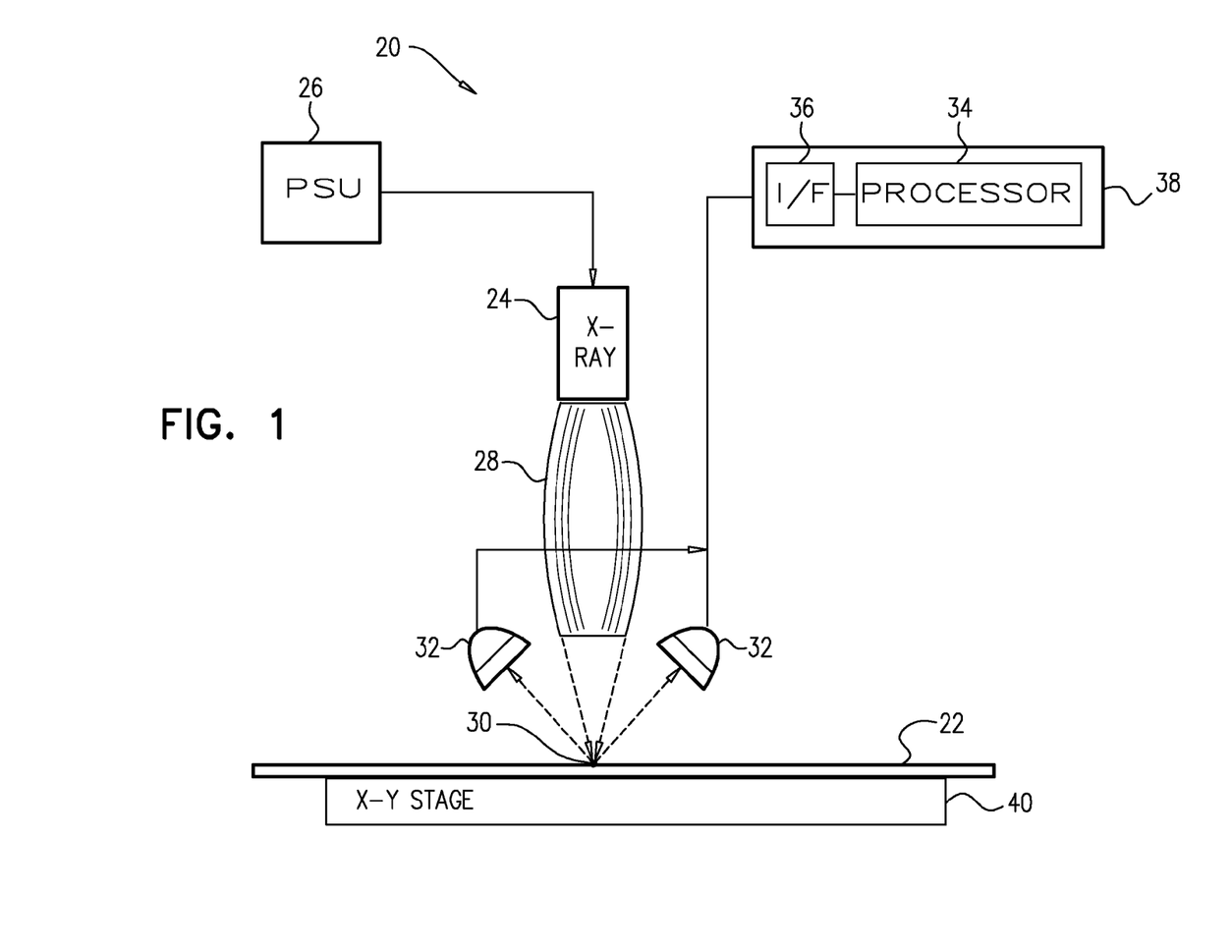
FIG. 1 is a schematic illustration of a system for X-ray fluorescence (XRF) measurement, in accordance with an embodiment of the present invention.

FIG. 1 is a schematic illustration of an X-ray microfluorescence system 20, in accordance with an embodiment of the present invention. Aspects of system 20 are described in detail in the above-mentioned U.S. Pat. No. 6,108,398. System 20 is arranged to inspect a semiconductor wafer 22 (or any other suitable sample), for example in order to identify faults in the wafer fabrication process, using methods described hereinbelow.

System 20 typically comprises an excitation source, such as an X-ray tube 24, driven by a high-voltage power supply unit (PSU) 26, as is known in the art. The X-ray tube emits X-rays having a suitable energy range and power flux into X-ray optics 28. The optics may comprise a polycapillary array, for example. Optics 28 focus the X-ray beam onto a small region 30, typically a spot on the order of 10-20 μm in diameter, on the surface of a sample 22. The irradiated region emits fluorescent X-rays, which are captured by a detector or by an array of detectors 32 arranged around region 30 and angled toward it. Responsively to the captured photons, detectors 32 generate electrical signals, which are conveyed to a signal processing unit 38. Unit 38 comprises a processor 34, which is configured to process the electrical signals, and an interface 36 for communicating the electrical signals from detectors 32 with processor 34.

The example of FIG. 1 refers to a specific configuration of an X-ray system. This configuration, however, is chosen purely for the sake of conceptual clarity. In alternative embodiments, the disclosed techniques can be used, mutatis mutandis, in various other types of fluorescence systems or analyzing modules known in the art, comprising any suitable excitation source, power source, focusing optics and detection system, may be used for implementing the methods described herein.

Processor 34 typically comprises an energy-dispersive pulse processing system, as is known in the art, which determines an intensity spectrum of the X-ray photons captured by the detectors. Alternatively, a wavelength-dispersive detection and processing system may be used. Each chemical element within the irradiated region that is excited by the X-rays from tube 24 emits X-rays in characteristic spectral lines. The intensity of the characteristic spectral lines of a given element is proportional to the mass of that element within region 30. Thus, processor 34 uses the determined intensity spectra to determine how much of a particular material is present within the area of region 30. Processor 34 typically comprises a general-purpose computer, which performs these functions under the control of suitable software. The software may be downloaded to the processor in electronic form, over a network, for example, or it may alternatively be provided on tangible media, such as optical, magnetic or electronic memory media.

As shown in FIG. 1, system 20 is used to examine region 30 on wafer 22. In one embodiment, the sample is mounted on a movable platform, such as an X-Y stage 40, so as to enable the sample to be moved with respect to the X-ray beam. Alternatively, the sample is mounted on a suitable stationary fixture while tube 24, optics 28 and detectors 32 are moved, so that the X-ray beam scans the wafer.

System 20 may be further configured to capture and process X-rays scattered from wafer 22 by other mechanisms, such as reflection, diffraction, and/or small-angle scattering. Multi-function systems of this sort are described, for example, in U.S. Pat. Nos. 6,381,303 and 6,895,075. The disclosures of these patents are incorporated herein by reference.

Estimating the Thickness and Composition of Thin Layers

Figure 2A:
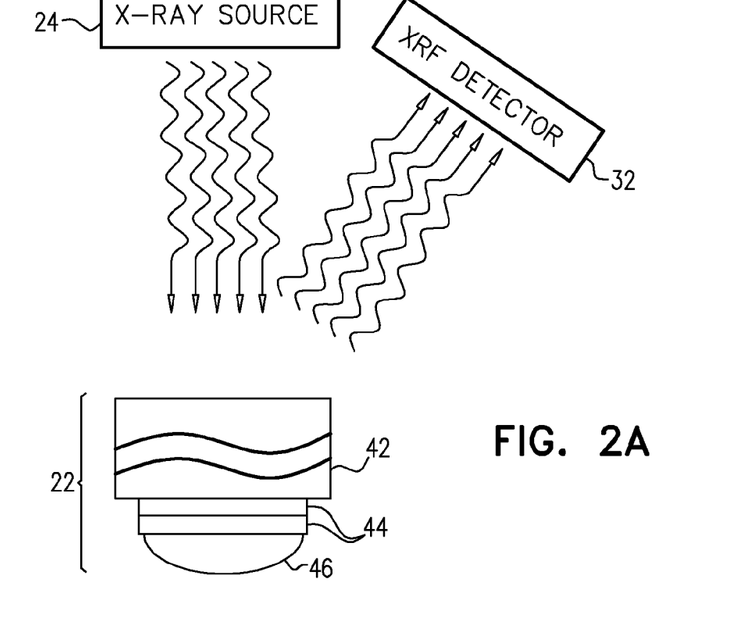
FIGS. 2A and 2B are schematic sectional views of a sample analyzed by the system of FIG. 1, in accordance with an embodiment of the present invention.

FIG. 2A is a schematic sectional view of sample 22 analyzed by system 20, in accordance with an embodiment of the present invention. Sample 22 represents one wafer in a typical stack of two or more semiconductor wafers packaged on top of each other using, for example, Wafer Level Packaging (WLP) technologies. For example, in face-to-face (FTF) WLP, two wafers are stacked such that a first wafer is faced-up and a second wafer is faced-down and positioned on top of the first wafer. Each wafer typically comprises an array of bumps that are formed on the wafer using a controlled-collapse chip connection (C4) manufacturing technology. Bumps may be formed on both the upper and lower surfaces of some wafers so as to connect between the semiconductor wafers in the WLP package.

Referring to FIG. 2A, sample 22 comprises a semiconductor wafer 42 (also referred to herein as a substrate), which is typically made of silicon and has a thickness on the order of 100 μm or less. An Under Bump Metallization (UBM) 44 is formed on the lower surface of wafer 42. UBM 44 comprises one or more layers, typically a stack of thin metal layers. Typically each layer is made of copper, nickel, palladium or gold, but other metals can also be used. A solder bump 46 is formed on UBM 44, and UBM provides electrical and physical (e.g., adhesion) connections between wafer 42 and bump 46. In the example of sample 22, solder bump 46 has a domed shape, however, the disclosed techniques are applicable with other kinds of bump materials and shapes, such as copper pillar bumps that are widely used in advanced WLP structures.

As described above, bumps are typically formed on both sides of wafer 22. FIG. 2A represents a manufacturing step that takes place before forming the UBM and bump on the upper surface of wafer 42. In some embodiments, tube 24 directs the X-ray beam through optics 28 onto region 30, and as a result, sample 22 excites XRF signals. Detectors 32 capture the excited signals. One or more detectors 32 are arrayed around sample 22, typically at equal elevations (about 45° in this example). Processor 34 computes spectral lines corresponding to the elements present in region 30, and derives the mass of each element within region 30 from the spectral-line intensities. The XRF spectrum obtained from the measurement of FIG. 2A is saved in processor 34 as a reference measurement to be used later to accurately estimate the mass, and thus the thickness, of each of the layers of a UBM 48, as will be shown and described in FIG. 2B below.

Figure 2B:
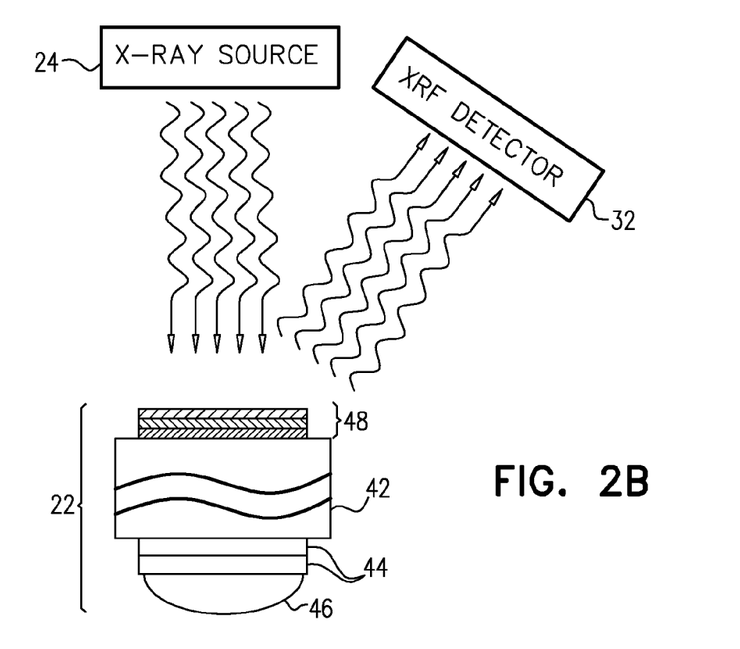

FIG. 2B is a schematic sectional view of sample 22 analyzed by system 20, in accordance with an embodiment of the present invention. Sample 22 comprises UBM 48 formed on the upper surface of wafer 22 in a next manufacturing process step to the one described in FIG. 2A. UBM 48 comprises one or more layers, typically a stack of thin metal layers that may be similar to the films of UBM 44. In other embodiments, the structure of UBM 48 is different than the structure of UBM 44, although the layers of UBM 48 may comprise similar elements to those of UBM 44 (e.g., copper, nickel and palladium).

Sample 22 is analyzed in system 20 by applying a similar XRF analysis procedure as described in FIGS. 1 and 2A. During the analysis of sample 22 of FIG. 2B, the X-ray beam impinges on sample 22 and XRF signals are excited from the metal layers of both UBMs 44 and 48. Since the output of detectors 32 comprises spectral lines originating from the metal layers of both UBMs 44 and 48, which are made of similar metals, processor 34 may not be able to distinguish between the signals excited from UBM 44 and those excited from UBM 48. In addition, UBM 48 attenuates some of the incident X-ray radiation of source 24 towards UBM 44, and also attenuates some of the XRF signals excited from UBM 44 towards the detectors.

Consequently, some of the spectral lines excited from UBM 44 are attenuated by UBM 48, and are different from the reference spectral lines that were acquired and saved in the reference XRF analysis of sample 22 (FIG. 2A), before the formation of UBM 48. As a result, processor 34 may not be able to isolate the net signal excited from UBM 48, and thus cannot accurately determine the thickness and/or composition of the layers of UBM 48.

The method described herein provides a technique to accurately determine the thickness of the layers of UBM 48 and has been demonstrated for micro-bump metrology WLP in the F2F WLP structure. The disclosed technique is additionally applicable for accurate determination of the elemental composition of the layers of UBM 48. The thin substrate in this case was a thinned device wafer with a thickness on the order of 100 μm or less. It can be appreciated, however, that the methods described herein are applicable in other situations, particularly in making measurements of small features that contain a particular element on both sides of a thin substrate.

In order to calculate the XRF spectral-line intensities of UBM 48, processor 34 may use Fundamental Parameters (FP) techniques, however, one should take into account the influence of the structure on the incident X-ray beam and the fluorescent x-ray beam. Rigorous mathematical treatment of such FP calculation are known in the art and further details of such mathematical treatments are described, for example, by B. Beckhoff, et al. in "Handbook of Practical X-Ray Fluorescence Analysis," Springer-Verlag, Berlin, Heidelberg, 2006, which is incorporated herein by reference; by D. K. G. de Boer, in "Calculation of X-Ray Fluorescence Intensities from Bulk and Multilayer Samples," X-RAY SPECTROMETRY, 19, 145-154, 1990; and by M. Mantler, in "X-ray fluorescence analysis of multiple-layer films," Analytica chimica acta, 188, 25-35, 1986, which are likewise incorporated herein by reference.

Equation 1 below provides an explicit expression for estimating the XRF intensity, Ii, of a given analyzed spectral line (denoted analyte line), i, in a multilayered structure, such as UBM 48:

$$I_i = f_i \cdot P(I_0, t_1, t_2, \ldots, t_n) \quad \text{Equation 1}$$

In Equation 1, $t_i$ is a thickness of a layer i, n is a number of layers, P is a function that takes into account the probabilities of interaction between the incident beam (intensity $I_0$) and the excited XRF beam with the multilayered structure, and $f_i$ is an empirical factor that takes into account all other factors, such as the system geometry, and a response function of detectors 32, that were not comprised in the P function.

In order to calculate the thicknesses $t_i$ of the layers 1 ... n of UBM 48 from the measured intensities, it is not possible to form a direct inverse function of function P. Since P is a non-linear function, finding its inverse can be done indirectly using an iterative calculation, for example as described by D. K. G. de Boer, et al., in "How Accurate is the Fundamental Parameter approach? XRF Analysis of Bulk and Multilayer Samples," X-RAY Spectrometry, Volume 22, Pages 33-38, 1993, which is incorporated herein by reference.

The disclosed techniques provide a method and system for extracting the layers thickness and/or composition from a model that takes into account only the XRF signal from the feature on the front of the substrate and treats the XRF intensities contributed by the backside of the substrate as a background signal that should be measured separately.

The methods described herein rely on two measurements: the first measurement, taken before forming UBM 48, as described in FIG. 2A, and denoted a background or reference measurement (the terms "background" and "reference" are used interchangeably in the present disclosure). The second measurement is conducted after forming UBM 48, as described in FIG. 2B and is referred to as a target measurement. Some disclosed embodiments use a modified version of the FP algorithm to find the contribution of the background signal to the intensity of the XRF spectral lines excited from UBM 48.

In order to estimate the background contribution (denoted $I_i^{Background}$) to the intensity of a given spectral line i (denoted $I_i^{Measured}$) measured after the formation of UBM 48, one may calculate the attenuation of the background by UBM 48. Note that there are some conditions in which the excited background XRF may not be attenuated by UBM 48. For example, when detectors 32 are positioned in an angle of 45° relative to the incident beam, as illustrated in FIGS. 2A and 2B, and when UBM 48 is plated on wafer 42 having a thickness in the range 50-70 μm, and the typical transverse dimension (e.g., width) of the UBM is about 30 μm, which is larger than the typical diameter of the x-ray beam. Note that the exited beam is attenuated to lower intensities for thicker wafer 22 and/or wider UBM layers and should be taken into account.

Background Attenuation Approximation

As a first-order approximation, one may assume that the background is excited by a beam with an energy of $E = \kappa \cdot E_{edge}$, wherein $E_{edge}$ is the lower threshold of the XRF excitation energy. Typically, the factor κ is a number in the range 1-2. Thus, the contribution of the background to the measured intensity $I_i$ of a spectral line i, should be added to the intensity calculated from FP (as given by equation 1):

$$I_i^{Measured} = f_i \cdot P(I_0, t_1, t_2 \ldots t_n) + I_i^{AttenuatedBackground}(E) \quad \text{Equation 2}$$

wherein $$I_i^{AttenuatedBackground}(E) = I_i^{Background} \exp\left\{-\sum_{j=0}^{j<n} \mu_j(E) t_j\right\} \quad \text{Equation 3}$$

and wherein the expression $\mu_j(E)$ represents a mass attenuation coefficient of layer j at energy E.

The factor κ should be tuned empirically to suppress the non-linear attenuation of the incident beam. This may be conducted, for example, by fitting the calculated intensities to the measured intensities of a reference structure (e.g., an industry standard sample). Note that in equations 2 and 3 we assume that the XRF beam comprises a quasi-monochromatic beam. To accurately model the case of a polychromatic beam, the tube spectrum should be measured or modeled and then one should integrate the total intensity resulting from the tube spectrum. The term quasi-monochromatic relates to the mathematical approximation $E = \kappa \cdot E_{edge}$. The disclosed techniques are applicable for a monochromatic beam as well as for a polychromatic beam.

The thicknesses $t_i$ of UBM 48 layers i=1 . . . n are calculated by solving equations 2 and 3 iteratively. In the present invention we assume nominal layer thicknesses at the beginning of the iterative calculations in order to overcome possible numerical difficulties associated with an instantaneous attenuation approximation of the background. Thus, the background attenuation by UBM 48 is evaluated at a first iteration using assumed nominal thicknesses of the layers of UBM 48, rather than using the instantaneous thickness (as calculated in equation 3). Then, this evaluated background attenuation is substituted back into equation 2, and the layer thicknesses of the layers of UBM 48 are calculated by solving equation 2.

In a second iteration, the calculated thicknesses of each layer of UBM 48 (as obtained from equation 2) are applied into equation 3 so as to re-evaluate the background attenuation. The evaluated figure of the attenuated background intensity obtained from equation 3 is placed into equation 2

(instead of the nominal-thickness-based value in the first iteration) so as to calculate the thicknesses of UBM 48 layers at a higher accuracy. This iterative process is repeated until the difference between the calculated thicknesses from two successive steps diminishes to below a threshold C. At this point the thickness measurement is completed and the output thickness is conveyed into a Statistical Process Control (SPC) or into any suitable process control system.

Figure 3:
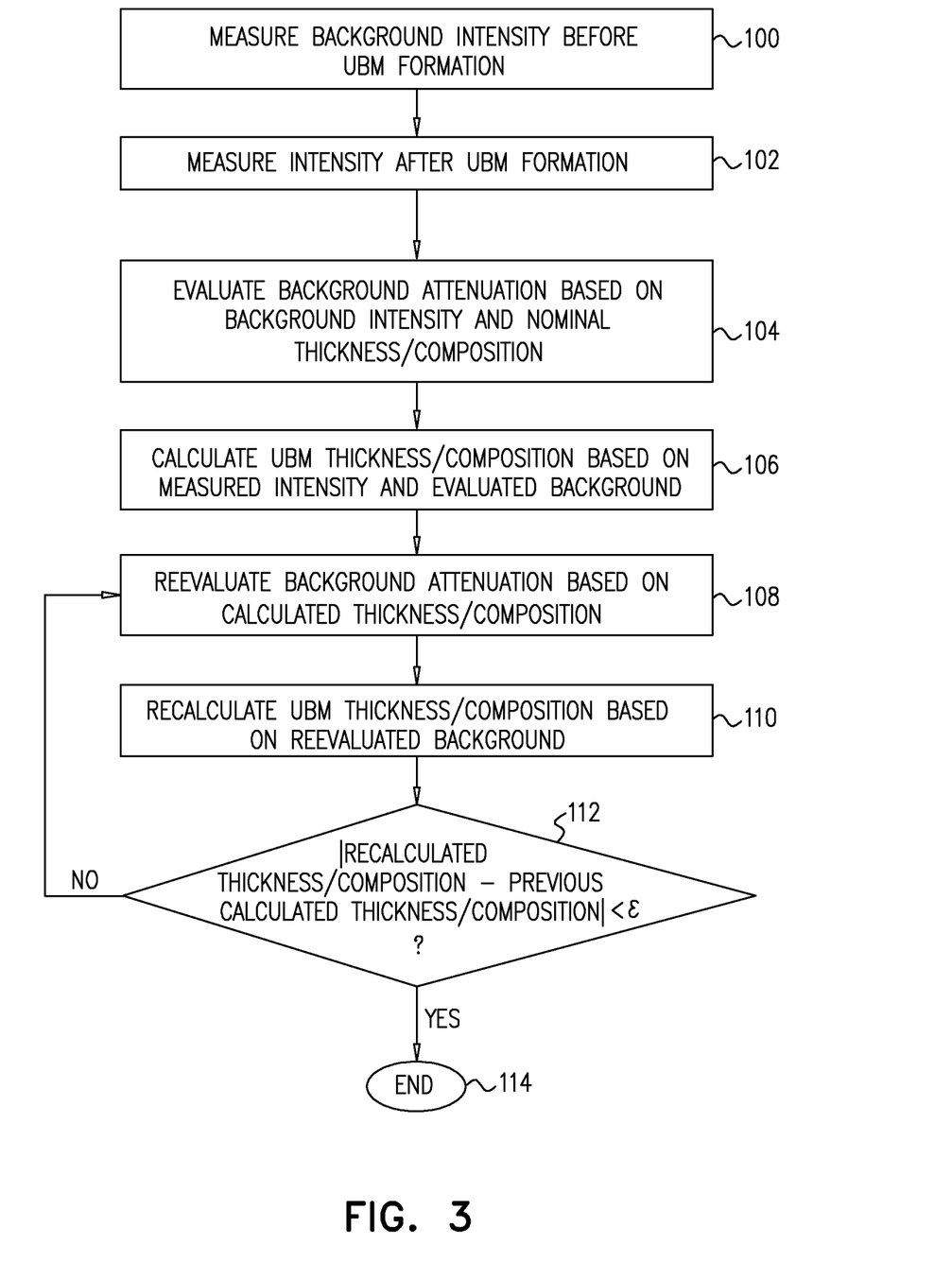
FIG. 3 is a flow chart that schematically illustrates a method for estimating the thickness and/or composition of Under Bump Metallization (UBM) layers using XRF analysis, in accordance with an embodiment of the present invention.

FIG. 3 is a flow chart that schematically illustrates a method for analyzing XRF so as to estimate thickness and/or composition of one or more layers of UBM 48, in accordance with an embodiment of the present invention. The term "UBM measurement" refers to measurement of one or more layers of interest in UBM 48, and the term "thickness" may be replaced with the term "elemental composition" since the disclosed technique is applicable for measuring the thickness and/or elemental composition of the analyzed layers. In addition, the disclosed method is applicable when using either a quasi-monochromatic beam approximation or accurate solution using appropriate polychromatic beam spectrum.

The method begins with system 20 measuring the intensities of one or more XRF spectral lines excited from sample 22 before the formation of UBM 48, at a background measurement step 100. At this manufacturing stage, UBM 48 is not formed on wafer 42 yet, so that the measured intensities of the XRF spectral lines represent background or reference intensities.

After the formation of UBM 48 on wafer 42, system 20 measures the intensities of the XRF spectral lines excited from sample 22 again, at a target measurement step 102. At a background evaluation step 104, processor 34 evaluates the background intensities of the various XRF spectral lines, which are attenuated by UBM 48. Processor 34 evaluates the background intensities using equation 3, based on assumed nominal thicknesses of the UBM 48 layers and the measured background intensity. At a thickness calculation step 106, processor 34 calculates the thickness of UBM 48 layers by feeding the measured intensities obtained at UBM measurement step 102, and the evaluated background, back into equation 2.

At a background re-evaluation step 108, processor 34 substitutes the calculated UBM thickness in equation 3 so as to re-evaluate the intensity of the attenuated background. The re-evaluated figure provides higher accuracy of the background intensities compared to background evaluation step 104, since the calculated thickness values are used instead of the assumed nominal values.

At a thickness recalculation step 110, processor 34 recalculates the thickness of UBM 48 by using the re-evaluated background in equation 2. The recalculated thickness at this stage is typically more accurate compared to the thickness calculated at thickness calculation step 106, due to higher accuracy of the background intensities used in this calculation.

The process described in the above four steps iteratively improves the accuracy of the calculated thicknesses of the layers of UBM 48 and is expected to converge. In some embodiments, in order to determine whether the iterative process has converged, and thus the obtained calculated thickness is sufficiently accurate, a convergence threshold value $\epsilon$ can be used.

At a comparison step 112, processor 34 compares the absolute value of the difference between the recalculated thickness (calculated at recalculation step 110) and the previously calculated thickness, to $\epsilon$. If the difference is greater than $\epsilon$, the process is not converged yet, and the method loops back to background re-evaluation step 108. If the absolute difference is smaller than $\epsilon$, the process is converged, the obtained thickness is final and the method ends, at an end step 114.

It will be appreciated that the embodiments described above are cited by way of example, and that the following claims are not limited to what has been particularly shown and described hereinabove. Rather, the scope includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for X-ray Fluorescence (XRF) analysis, comprising:
   directing an X-ray beam onto a sample;
   measuring an XRF signal excited from the sample, in a reference measurement in which the sample comprises one or more first layers formed on a substrate, so as to produce a reference XRF spectrum;
   re-measuring the XRF signal excited from the sample in a target measurement after one or more second layers are formed on the substrate in addition to the first layers, so as to produce a target XRF spectrum that comprises first spectral components contributed by the first layers and second spectral components contributed by the second layers;
   reducing a level of contribution of the first spectral components to the target XRF spectrum using the reference XRF spectrum; and
   estimating a parameter of at least one of the second layers using the target XRF spectrum in which the level of contribution of the first spectral components has been reduced.

2. The method according to claim 1, wherein the parameter comprises a thickness of at least one of the second layers.

3. The method according to claim 1, wherein the parameter comprises an elemental composition of at least one of the second layers.

4. The method according to claim 1, wherein the first and second layers are formed on respective first and second opposite surfaces of the substrate, such that the second surface faces the X-ray beam.

5. The method according to claim 4, wherein the contribution of the first spectral components to the target XRF spectrum is caused by excitation in the first layers by the X-ray beam after penetrating the substrate.

6. The method according to claim 1, wherein the first or second layers comprise Under Bump Metallization (UBM) layers or bumps.

7. The method according to claim 1, wherein reducing the level of contribution of the first spectral components comprises estimating a contribution of a first spectral line in the reference XRF spectrum to an intensity of a second spectral line in the target XRF spectrum that overlaps the first spectral line.

8. The method according to claim 7, wherein estimating the contribution of the first spectral line comprises estimating an attenuation of the first spectral line by the second layers.

9. The method according to claim 8, wherein estimating the attenuation comprises iteratively evaluating the attenuation as a function of respective estimated parameters of the second layers.

10. The method according to claim 9, wherein iteratively evaluating the attenuation comprises, in an initial iteration, evaluating the function using nominal parameters of the second layers.

11. An apparatus for X-ray Fluorescence (XRF) analysis, comprising:
an X-ray source, which is configured to direct an X-ray beam onto a sample;
a detector, which is configured to measure an XRF signal excited from the sample in a reference measurement in which the sample comprises one or more first layers formed on a substrate, and to re-measure the XRF signal excited from the sample in a target measurement after one or more second layers are formed on the substrate in addition to the first layers; and
a processor, which is configured to produce a reference XRF spectrum from the reference measurement, to produce from the target measurement a target XRF spectrum that comprises first spectral components contributed by the first layers and second spectral components contributed by the second layers, to reduce a level of contribution of the first spectral components to the target XRF spectrum using the reference XRF spectrum, and to estimate a parameter of at least one of the second layers using the target XRF spectrum in which the level of contribution of the first spectral components has been reduced.

12. The apparatus according to claim 11, wherein the parameter comprises a thickness of at least one of the second layers.

13. The apparatus according to claim 11, wherein the parameter comprises an elemental composition of at least one of the second layers.

14. The apparatus according to claim 11, wherein the first and second layers are formed on respective first and second opposite surfaces of the substrate, such that the second surface faces the X-ray beam.

15. The apparatus according to claim 14, wherein the contribution of the first spectral components to the target XRF spectrum is caused by excitation in the first layers by the X-ray beam after penetrating the substrate.

16. The apparatus according to claim 11, wherein the first or second layers comprise Under Bump Metallization (UBM) layers or bumps.

17. The apparatus according to claim 11, wherein the processor is configured to reduce the level of contribution of the first spectral components by estimating a contribution of a first spectral line in the reference XRF spectrum to an intensity of a second spectral line in the target XRF spectrum that overlaps the first spectral line.

18. The apparatus according to claim 17, wherein the processor is configured to estimate the contribution of the first spectral line by estimating an attenuation of the first spectral line by the second layers.

19. The apparatus according to claim 18, wherein the processor is configured to estimate the attenuation by iteratively evaluating the attenuation as a function of respective estimated parameters of the second layers.

20. The apparatus according to claim 19, wherein the processor is configured to evaluate the function in an initial iteration using nominal parameters of the second layers.

* * * * *